United States Patent [19]
Hillman et al.

[11] Patent Number: 5,697,899
[45] Date of Patent: Dec. 16, 1997

[54] FEEDBACK CONTROLLED DRUG DELIVERY SYSTEM

[75] Inventors: Robert S. Hillman; Christian P. Valcke; Robert T. Gauthier, all of San Diego, Calif.

[73] Assignee: Gensia, San Diego, Calif.

[21] Appl. No.: 386,916

[22] Filed: Feb. 7, 1995

[51] Int. Cl.⁶ ................................................ A61M 1/00
[52] U.S. Cl. ............................................................ 604/28
[58] Field of Search ........................... 604/28, 31, 53, 604/65, 67, 131, 183, 186, 257

[56] References Cited

U.S. PATENT DOCUMENTS

| | | | |
|---|---|---|---|
| 4,280,494 | 7/1981 | Cosgrove . | |
| 4,526,568 | 7/1985 | Clemens et al. | 604/28 |
| 4,673,386 | 6/1987 | Gordon | 604/48 |
| 4,767,399 | 8/1988 | Bollish | 604/28 |
| 4,769,001 | 9/1988 | Prince | 604/28 |
| 5,134,079 | 7/1992 | Cusack et al. | 422/81 |
| 5,324,266 | 6/1994 | Ambrisco et al. | 604/125 |
| 5,374,401 | 12/1994 | von Berg | 422/101 |
| 5,390,552 | 2/1995 | Demachi et al. | 73/863.73 |

FOREIGN PATENT DOCUMENTS

| | | |
|---|---|---|
| 0357466 | 3/1989 | European Pat. Off. . |
| 0510722 | 3/1989 | European Pat. Off. . |

OTHER PUBLICATIONS

Biostator GCIIS Brochure entitled "Rapid–Feedback Blood Glucose Control", Miles Laboratories, Inc., 1980.
Biotrack 512 Coagulation Monitor Specifications Brochure, CIBA Corning, 1991.
Via Medical Corporation Brochure entitled "Real Time Blood Chemistry Monitoring", 1993.
Mungall, Dennis R., et al., "A Prospective Randomized Comparison of the Accuracy of Computer–Assisted Versus GUSTO Nomogram–directed Heparin Therapy", Clinical Pharmacology & Therapeutics, May, 1994, pp. 591–596.

Kershaw et al., "Computer–Assisted Dosing of Heparin, Management With a Pharmacy–Based Anticoagulation Service", Archives of Internal Medicine, May 9, 1994, pp. 1005–1011.

Jannett, T.C. et al., "Simulation of Adaptive Control of Anticoagulation During Hemodialysis", Biomedical Applications of Automatic Control, Proceedings from the Annual International Conference of the IEEE Engineering in Medicine and Biology Society, vol. 13, No. 5, 1991, pp. 2147–2148.

Frucht et al., "Computer–Assisted Blood Pressure Control By Cardiovascular Drugs –Problems in Developing a Closed Loop Control System", Anasth. Intensivther. Notfallmed. 21 (1986).

*Primary Examiner*—Max Hindenburg
*Attorney, Agent, or Firm*—Lyon & Lyon LLP

[57] ABSTRACT

A feedback controlled drug delivery system includes automated blood sampling and analysis and dosing of the patient. Automated sampling is performed by direct analysis of patient blood, such as for measurement of its coagulation state. A novel manifold includes a fluid input port, a patient port adapted to output fluid and to receive a blood sample from the patient, and a fluid pathway connecting the fluid port and the patient port. A sample line is connected to the fluid pathway to provide the sample to an analyzer. In one aspect of this invention, the sample is forced through the sample line by isolating the patient port, such as by a valve, and non-drug fluid is forced into the manifold causing the blood to cross through the sample line. Alternately, a pump force may be utilized on the sample line. In another aspect of this invention, a positive interlock system is utilized between a drug source and the system. In yet another aspect of this invention, a improved multitest unit is provided, such as in a carousel or stacked manner.

17 Claims, 7 Drawing Sheets

FEEDBACK CONTROLLED DRUG DELIVERY SYSTEM

FIELD OF THE INVENTION

This invention relates to the field of feedback controlled drug delivery system. In other aspects, this invention relates to systems for the automatic sampling of the patient sample or state. More particularly, this invention relates to the field of automatic monitoring systems used in conjunction with variable dose drug delivery systems, especially those for use with drug administration which otherwise requires a high degree of monitoring by healthcare professionals.

BACKGROUND OF THE INVENTION

A wide variety of drug delivery systems are known to the art, ranging from systems totally relying upon the healthcare professional for dosing decisions and administration to highly automated systems performing one or more tasks such as monitoring, analyzing, dosing decisions and dosing.

At the nonautomated, simplest end of the spectrum, a drug delivery system may comprise a preset regimen performed at a preset infusion rate without feedback, such as when a patient is given a prescribed dosing regimen. At a higher level of control, feedback systems are utilized in which analysis of the patient's current condition is utilized in a feedback controlled manner as input for the dosing analysis. These steps may be performed by the healthcare professional with or without the use of automation or computational tools.

Example of a nomogram based, nonautomated drug delivery system includes various heparin delivery systems now in wide spread use. Other such systems use hirudin, hirulog and other direct thrombin inhibitors. Heparin is a well known anticoagulant used to avoid clotting, such as during dialysis, thrombolytic therapy, acute unstable angina, cardiac catherization, coronary artery bypass surgery, stent placement and PTCA, pulmonary embolism, deep vein thrombosis, treatment of transcient ischemic attack and stroke. At certain intervals, blood is drawn from the patient, and analyzed for its coagulation ability. Although heparin is generally viewed as a relative safe and efficacious drug, it may result in an increased risk of hemorrhage, and has proved difficult to select ideal heparin dosage. There is a wide variation in patient-to-patient response, both in the heparin concentration which results from a given heparin infusion rate, and in the patient response to a given heparin concentration. Nonautomated control is difficult and often imprecise.

Various commercially available analysis units are available to analyze a small amount, e.g., a drop, of patient blood to determine the coagulation state of the blood. Based upon this analysis, dosing decisions are made ad hoc or with the aid of a nomogram. The heparin is then administered to the patient based on this decision.

Various proposals have been made to automate the dosing decision step in the heparin delivery. In Dennis R. Mungall, et al., "A Prospective Randomized Comparison of the Accuracy of Computer-Assisted Versus GUSTO Nomogram-directed Heparin Therapy", Clinical Pharmacology & Therapeutics, May, 1994, pp 591–596, a computer system utilized the activated partial thromboplastin time (APTT) measured on a preset interval as input to determine dosing decisions. A Bayesian forecasting computer program was utilized, assuming a non-linear pharmakinetic model for heparin. Initial estimates of heparin requirements were based on prior knowledge of demographic characteristics, specifically weight, sex, and current smoking condition. Similarly, in Kershaw et al., "Computer-Assisted Dosing of Heparin, Management With a Pharmacy-Based Anticoagulation Service", Archives of Internal Medicine, May 9, 1994, pp 1005–1011, a computer-assisted dosing of heparin was performed. APTT measurements were used as the input to the system. Finally, specific work has occurred in an attempt to optimize drug delivery where sparse measurements are available. See, e.g., T. C. Jannett et al., "Simulation of Adaptive Control of Anticoagulation During Hemodialysis", Biomedical Applications of Automatic Control, Proceedings from the Annual International Conference of the IEEE Engineering in Medicine and Biology Society, Vol. 13, No. 5, 1991, pp 2147–2148.

Various adaptive control system have been proposed. These systems attempt to utilize data obtained historically and from individual patient response as input to the control system determining drug dosing. These adaptive control systems have particular applicability to delivery systems in which sparse measurements are available. One proposed system by Jannett et al., above, utilizes a model based system with parameter estimation. Sparse measurements, at infrequent or differently timed intervals, are utilized in an attempt to estimate appropriate drug delivery.

At a higher level of integration, various automated drug delivery systems are known to the art. Relatively simple systems utilizing noninvasive monitoring systems monitor a patient variable and provide dosing based upon decisions made by a control system in a feedback controlled manner. For example, automated blood pressure monitoring systems exist. Automated blood pressure measurement devices are automatically activated, typically at preset time intervals, which cause the increase in cuff pressure on an automated blood pressure measurement system, and then the detection of the patient's blood pressure. These systems generally attempt to hold the patient at a preset level, such as a desired blood pressure level. See, e.g., Cosgrove Jr., et al. U.S. Pat. No. 4,280,494, or at a higher level of complexity attempt to mimic the natural variations in a patient's physiologic variable, such as a circadian rhythm in blood pressure. See, e.g., Frucht et al., "Computer-Assisted Blood Pressure Control By Cardiovascular Drugs—Problems in Developing a Closed Loop Control System", Anasth. Intensivther. Notfallmed. 21 (1986).

Yet another noninvasive, feedback controlled system is the GenESA system of Gensia, Inc. which monitors a patient's heart rate as a control input for a system which causes delivery of a exercise simulating agent, such as arbutamine, so as to mimic the effects of aerobic exercise. In one application, such system may be utilized to perform a cardiac stress test on patients, such as by varying the cardiac stress as a function of time.

The control of certain physiologic parameters requires the invasive monitoring of the patient, such as in systems requiring direct analysis of the patient's blood. A system from VIA Medical automatically draws and analyzes patient blood. A delivery set is connected to the patient's vein which is utilized for the dual function of fluid delivery, such as a physiologic solution, and blood withdrawal from the patient. A pump is used to draw the blood from the patient through the delivery set. Analysis occurs by drawing the blood through a closed circuit which contains a sensor in-line. Sensors external to the patient measure various analytes in the blood. In suggested operation, the blood drawn from the patient is reinfused to the patient.

Yet another blood analysis system is that shown in Cusack U.S. Pat. No. 5,134,079. A fluid sample collection system utilizes a patient sample, such as blood, with an immiscible fluid, such as air, and a washing fluid, such as saline, to segment portions of the patient sample and to transport them to an analyzer. The blood and saline are connected by a fluid path, which in combination forms a transfer tube to pass the blood and saline alternately to the analyzer. From a fluidics standpoint, the patient sample and the immiscible fluid are input from separate input ports which form a Y-connection with the fluid path towards the analyzer. A third input port forms a T-connection with the fluid path and provides input for the immiscible fluid to the fluid path. A downstream pump causes motion through the fluid path tube. A detector is positioned downstream of the pump but upstream of the output port to the analyzer. In each of the modes of operation described, segmentation of the blood is required. No provision is made for return of the sampled blood to the patient which is not used in the analysis.

Various blood gas measuring systems are known in the art, some of which are noninvasive and some of which are invasive. One such system is made by FOxS Systems which comprises an inter-arterial blood gas system which measures pH, $PCO_2$, $pO_2$, and temperature on a continuous basis. The system uses optical fluorescent sensors optimized for each analyte of interest. A system by Diametrics performs blood gas analysis utilizing a small cartridge inserted into the front of an IRMA analyzer. After a calibration step, arterial blood is injected into the cartridge which performs the analysis.

The Biostator™ system of Miles Laboratories is an automated, invasive feedback controlled drug delivery system. One line connects the patient in a closed circuit serving to provide fluid delivery, such as saline, to the patient as well as to sample blood from the patient. The sampled blood is then analyzed to determine the glucose concentration, which is used to calculate an insulin infusion rate to control the blood glucose level.

While much progress has been made in the general field of automated, feedback controlled drug delivery, deficiencies remain for certain applications. Current systems for therapeutic dosing are often time consuming, requiring the direct input of a healthcare professional. Automatic analysis is often difficult or impossible and requires substantial skill and training on the part of the healthcare professional. Under such circumstances, it is difficult to perform such therapeutic dosing in a non-hospital environment, such as for in-home healthcare. Further, given the multiple step and complex nature of the measurement, analysis and dosing steps, errors can occur in any one of these steps and cause a cumulative effect, causing risk for the patient. Further, a high degree of control is often required, especially for administration of anticoagulants, where the therapy has a narrow therapeutic index (i.e., too low a dose will result in decreased efficacy such as reoccurrence of deep vein thrombosis (DVT) and too high a dose will result in side effects (such as bleeding and hemorrhagic stroke). Current practice requires a multiple step operation, with each step incurring the potential for error. Generally, these steps are as follows: the patient is hooked to the heparin IV unit, a bolus of heparin is administered, a sample is drawn and sent to the lab, the lab analyzes the sample for aPTT value, the nurse receives the results, with a possible delay of upwards of 1 hour, the heparin dose is determined based on the physician's order or by using a nomogram, the IV pump is adjusted with the new heparin rate and the next sample time is determined. Cumulative errors can result in suboptimal delivery rates.

Despite the numerous attempts to provide a more automated and reliable system for drug delivery, no satisfactory solution has been proposed for systems requiring invasive monitoring of patient blood and subsequent control of anticoagulant effects.

SUMMARY OF THE INVENTION

The invention comprises a feedback controlled drug delivery system particularly adapted for performing automated blood analysis, computing optimal dosage and controlling a drug delivery system to administer the dose to the patient. The sampling methods and apparatus, the control system and the drug delivery interconnect all include novel aspects of this invention. In the preferred embodiment, this invention is utilized with a feedback controlled drug delivery system requiring automated withdrawal and analysis of patient blood, such as for its coagulation state, and determination of the optimal dosage to be delivered. That optimal amount is calculated for a system having infrequent measurements, and then drug delivery, such as of an anticoagulant, is administered.

From a system standpoint, one or more sources of drug are provided to the patient in a controlled manner such as from delivery through a pump system. Control of the pumps is performed by a control system which utilizes the measured patient variable as input information.

Structurally, one or more drug sources and, optionally, a source of fluid, e.g., saline, are operatively connected to pumps to control the flow rates to the patient. A novel manifold interconnects the patient, the saline source and the analyzer. The manifold includes an input port adapted to receive a fluid, e.g., saline or drug, a patient port adapted to output fluid to the patient and to receive blood from the patient, a fluid pathway connecting the saline port and the patient port, and a sample line connected to the fluid pathway, the sample line having an input connected to the fluid pathway and an output directed towards the analyzer. A pump force path is connected to the fluid pathway at a point between the saline port and the sample line, and is adapted to provide a pumping force on the fluid pathway. Optionally, a detector position between the pump force port and the access to the analyzer serves to detect the interface between blood and a more transparent fluid, such as saline.

In operation, the manifold may be operated so as to sample the patient blood from a portion of the slug or discrete volume of blood displaced from the leading edge of the slug. In the preferred mode of operation, the saline delivery to the patient occurs in normal operation through the fluid pathway of the manifold. To obtain a blood sample, the saline source is disconnected from the fluid pathway, such as by operation of a poppet valve, followed by activation of the pumping force, thereby causing the saline in the fluid pathway to be drawn towards the pump force. This fluid flow in turn causes the patient blood to be drawn from the patient through the patient port of the manifold and through the fluid pathway. Once the blood has been pulled through the fluid pathway to a position past the intersection of the path to the analyzer, such as preferably determined by the detector, the blood slug will present a nonleading edge at the opening of the access to the analyzer. Blood from the nonleading edge of the slug may then be delivered to the analyzer. In the preferred embodiment, the blood is pushed towards the analyzer through the analyzer pathway, preferably by closing a valve at the patient port, driving fluid, e.g., saline, into the input port of the manifold, the resultant action being that the nonleading edge of the blood slug is forced towards the analyzer. Alternatively, a pumping force may draw the blood towards the analyzer.

In another aspect of this invention, a computer controlled system utilizes discrete, often sparse, sample data as input to the control system. Optionally, the patient's dosing history and/or response may be utilized in the control system. Expert systems may be utilized, especially for drugs which are difficult to administer. The control system outputs dosing information to the drug delivery device.

Analysis systems previously requiring individual test cartridges for a single test are combined in a multiple unit arrangement. In one embodiment, a carousel comprising multiple individual test units permits rotational motion of the test units beneath a source delivery location. In another embodiment, multiple individual test units are bundled in a stack arrangement, the new units being used on or taken from the stack as needed.

In yet another aspect of this invention, an interlock system is utilized to cooperatively and positively couple and interlock a drug source, e.g., heparin, to an input to the remainder of the drug delivery system. Optionally, the interface includes a system disable, such that if an unauthorized drug source is attempted to be used with the system, the system is disabled. In this way, a defined source of heparin may be used to minimize heparin variability and patient variability.

Accordingly, it is an object of this invention to provide an automated, feedback controlled drug delivery system capable of use with drugs which require a high degree of patient monitoring.

It is yet a further object of this invention to provide an improved apparatus and method for automatic sampling of blood for use in an extracorporial circuit and analyzer.

It is a object of this invention to provide an improved device for use in the acute and home care drug delivery field.

It is yet a further object of this invention to provide an automated titration of drug based upon an automated measurement of a patient parameter.

It is yet a further object of this invention to provide a system useful with antiplatelet aggregation assays.

It is yet a further object of this invention to provide an improved system for the optimized delivery of a drug to maximize therapeutic benefit.

In yet another aspect of this invention, a novel arrangement of test cartridges is utilized for the analyzer.

DETAILED DESCRIPTION OF THE INVENTION

Figure 1:
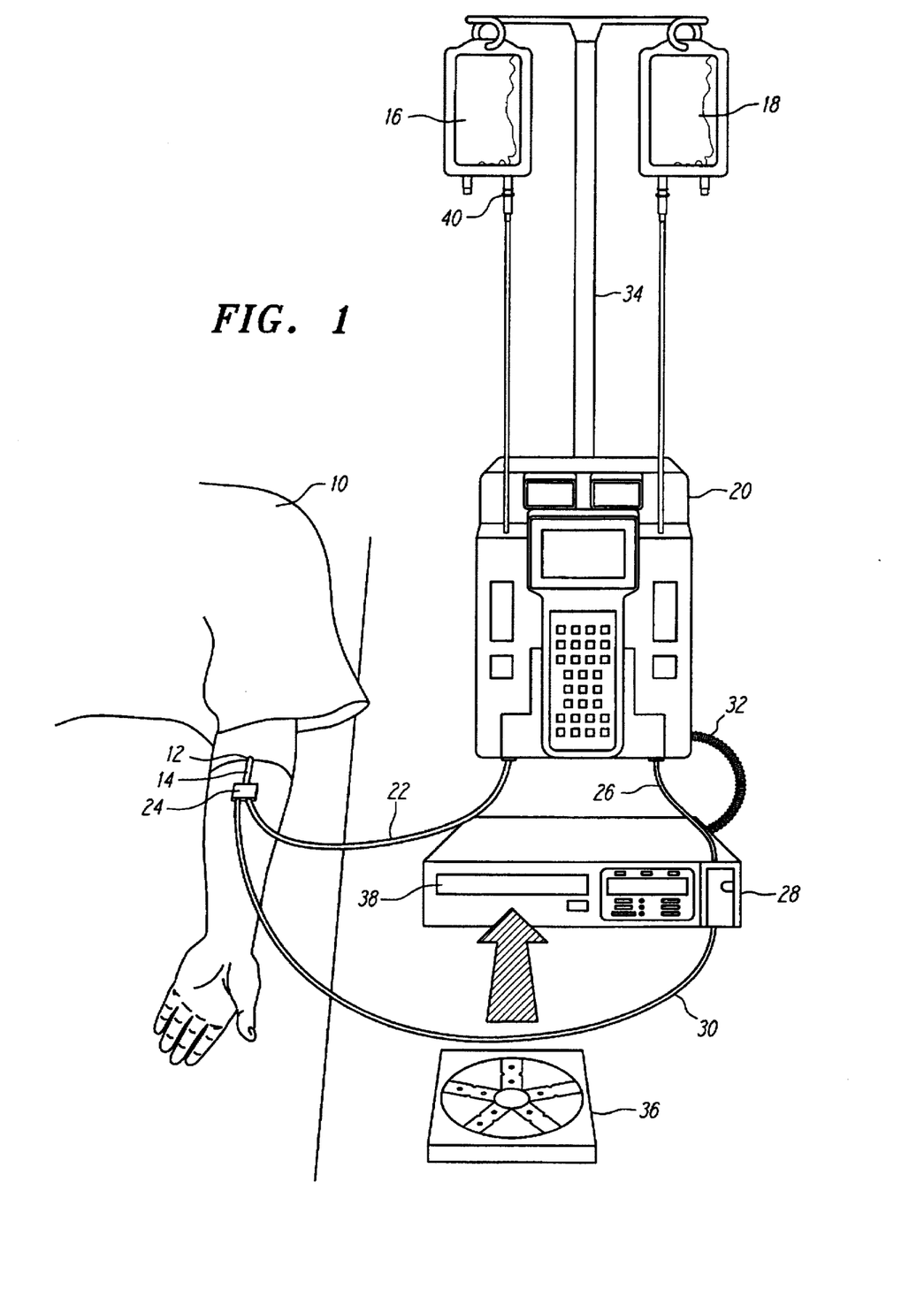
FIG. 1 shows a perspective view of the feedback controlled drug delivery system in one embodiment.

FIG. 1 shows a perspective view of the components of this invention in one preferred embodiment. A patient 10 is coupled to the system via a multiple lumen catheter (not shown) accessing a patient vein at access point 12. The preferred catheter is one from Arrow-Twin Cath®. One or more drug sources 16 and fluid source 18, such as saline, are connected to a pump system 20. The pump system preferably is capable of controlling fluid flow from the drug source 16 and the fluid source 18. The delivery of the drug to the patient 10 occurs through drug delivery tube 22 as measured and monitored by the pump 20. The delivery tube 22 is connected to one lumen of the multiple lumen catheter. The output of the fluid source 18 as measured and pumped by pump 20 is output via fluid delivery tube 26 to the analysis and control system 28. A tube 30 provides connection between the analysis and control system 28 and the patient 10, preferably through a different lumen of the multiple lumen catheter. The tube 30 preferably provides bidirection fluid flow, providing transfer from the fluid source 18 to the patient 10 of the fluid, e.g., saline, and at alternate times, transfer of the patient sample, such as blood from the patient 10 to the analysis and control system 28. The analysis and control system 28 provides control signals to the pump 20 via connection 32. The pump 20 and analysis and control system 28 may be conveniently disposed on a conventional rack 34.

The analysis and control system 28 is shown as a single integrated unit, though it may be formed into one or more components as desired. The analysis and control system 28 as shown is adapted to receive a multiple test unit 36 as inserted into a receiving slot 38. A directional arrow shows the action of insertion of the multiple test unit 36 into the receiving slot 38.

In one aspect of this invention, an interlock system 40 is utilized to provide an interface between the drug source 16 and the pump 20. The interlock system 40 is adapted to provide limited interconnection between authorized drug sources 16 and the remainder of the system. The interlock system 40 may include mechanical interlock features and/or electrical interlock features.

Figure 2:
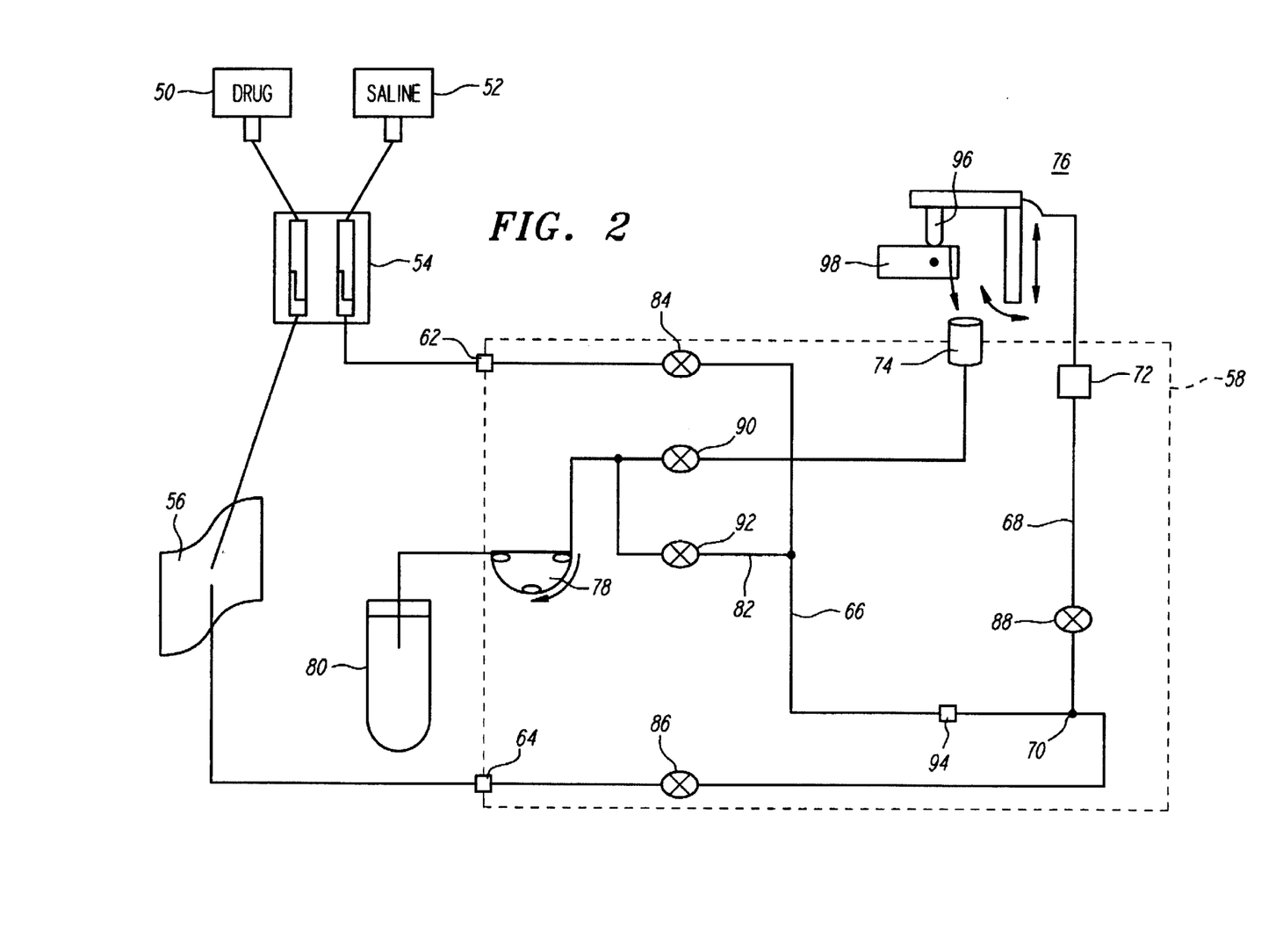
FIG. 2 shows a schematic diagram of the fluidic system in one embodiment.

FIG. 2 shows a schematic version of one fluidic system in accordance with this invention. A drug source 50 and fluid source 52 are connected via fluid pathways to the IV pump system 54. Preferably the IV pump system 54 is a multi-channel IV pump system adapted to regulate flow from the various sources, such as potential multiple drug sources 50 and fluid sources 52. The patient arm 56 is in fluidic contact with the IV pump system 54 for delivery of the drug from drug source 50. A manifold 58 is shown included within the dashed lines. The manifold includes a fluid port 62 adapted to receive output of the fluid source 52 as regulated by the IV pump system 54. A patient port 64 provides connection to the patient arm 56 via a tube comprising a fluidic connection. The patient port 64 alternately provides output of fluid initiating at the fluid source 52 to the patient arm 56, and at alternate times, receives blood from the patient arm 56 as input to the manifold 58. The fluid port 62 is connected to the patient port 64 via a fluid pathway 66. A sample line 68 is connected to the fluid pathway 66. Preferably, the sample line 68 forms a T-intersection with the fluid pathway 66 at intersection node 70. The sample line 68 provides fluidic transport of materials from the fluid pathway 66 to an analysis system. Optionally, the sample line 68 terminates in an analyzer interface port 72. Optionally, a disposal port 74 may be provided as input to the manifold 58 adapted to receive waste output from the analyzer 76.

Transfer of fluids through the manifold 58 is controlled by operation of the IV pump system 54 and additional pump forces. Such additional pump forces may be provided by a pump 78 or, in the alternative or in addition thereto, a vacuum source 80. In this embodiment, the pump force is supplied so as to selectively receive materials from the disposal port 74 and the fluid pathway 66. The pump force is supplied to the fluid pathway 66 via a pump connection 82. The pump connection 82 preferably forms a T-connection with the fluid pathway 66. The fluid flow within the manifold is also controlled by operation of valves. A upstream isolation valve 84 is preferably disposed on the fluid pathway within the manifold 58 downstream of the fluid port 62. A patient shut-off valve 86 is preferably located in the fluid pathway 66 upstream of the patient port 64 and downstream of sample line 68. A analyzer access valve 88 is preferably disposed adjacent the intersection node 70, preferably on the sample line 68. A disposal valve 90 is interposed between the disposal port 74 and the pump force source. A pump force valve 92 is disposed between the pump force and the fluid pathway 66, optionally with some section of the pump connection 82 disposed between the pump force valve 92 and the fluid pathway 66.

In one aspect of this invention, a detector 94 is preferably positioned to determine the position of fluid or blood within the manifold 58. In the preferred embodiment the detector 94 is positioned adjacent the fluid pathway 66 between the upstream isolation valve 84 and the intersection node 70. More particularly, if a pump force is supplied directly to the fluid pathway 66, as shown, the detector 94 is preferably positioned between the intersection of the pump connection 82 and the intersection node 70. Any form of detector 94 consistent with the objects of this invention may be utilized. The preferred detector utilizes optical changes in the contents of the fluid pathway 66 to detect a change. For example, an optical detector 94 may detect the blood/saline interface when that interface is adjacent the detector 94. An ultrasonic detector may be used to detect the presence of fluid in line 66.

In operation, the system may be operated wherein the patient receives fluid, such as saline, from the fluid source 52. In that event, the fluid is received at the fluid port 62 and transferred through the fluid pathway 66 and output at the patient port 64 with valves 84 and 86 being open. Ordinarily, this may occur simultaneously with infusion of the drug from the drug source 50. To perform a measurement, drug flow is preferably terminated, so as to permit more accurate reading of the patient state. To sample blood from the patient, the upstream isolation valve 84 is closed and the pump force applied to the fluid pathway 66. In the disclosed embodiment, the pump 78 provides a pumping force on pump connection line 82 via now opened pump force valve 92. This causes the sample to be drawn through the patient port 64 past now opened patient shut-off valve 86. The pump 78 provides the removed saline to the disposal container 80. The blood is drawn at least to intersection node 70, and preferably to detector 94. Once sufficient blood has been drawn, the blood is then taken from the intersection node 70 through the sample line 68 to the analyzer 76. In one embodiment, the blood is pushed through the sample line 68 by closing the patient shut-off valve 86, opening the analyzer access valve 88, closing the pump force valve 92 and opening the upstream isolation valve 84. This combination permits material from the fluid source 52 to be pumped by IV pump system 54 through the upstream portion of fluid pathway 66 to cause flow of the blood slug up through the sample line 68. Advantageously, if the blood slug has a leading edge disposed upstream of intersection node 70, the blood in the sample line 68 is taken from the non-leading edge of the blood slug in the fluid pathway 66. Alternatively, the blood may be drawn from intersection node 70 by a pump force applied to sample line 68 directed towards analyzer interface port 72. In the embodiment shown, analyzer 76 receives a blood sample from the analyzer interface port 72. A sample nozzle 96 serves to deliver the blood to the test unit 98. Optionally, the sample nozzle 96 may be placed in apposition to the disposal port 74 to dispose of the leading edge of the blood slug which travels through sample lines 68. The sample nozzle 96 may then deliver a clean blood sample to the test unit 98. After the blood is delivered to the test unit 98, the manifold 58 may be flushed with saline, serving also to clean the sample nozzle 96. Disposal of this material from the sample nozzle 96 is via the disposal port 74. The remaining patient blood in the manifold and connection from the patient port 64 to the patient arm 56 may be returned to the patient.

Figure 3:
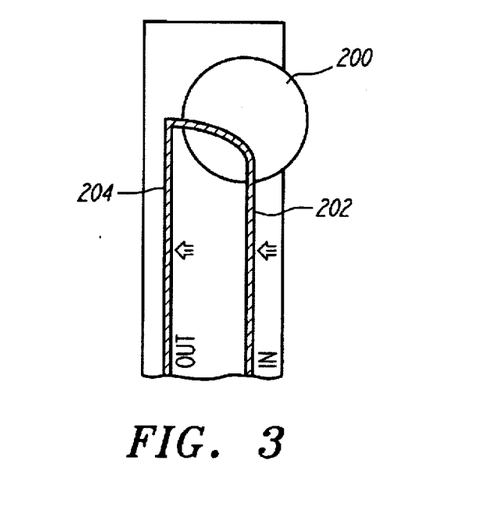
FIG. 3 is a planned view of a switch useful to alternately deliver blood to the analyzer or to a second output.

FIG. 3 shows a planned view of a valve arrangement which permits selective delivery of the blood sample to an analyzer or to the continuation of a blood circuit. A rotational valve 200 receives as input from path 202 a blood sample. In one orientation of the rotation valve 200, the pathway 202 is connected to an output path 204. When the rotational valve 200 is rotated 90° (counter-clockwise in FIG. 3) the rotational valve 200 provides connection from the pathway 202 to the analyzer (not shown). By rotation of the valve 200, blood may be directed to the analyzer (such as an aPPT cartridge) or to a waste cartridge by a simple rotation.

Figure 4:
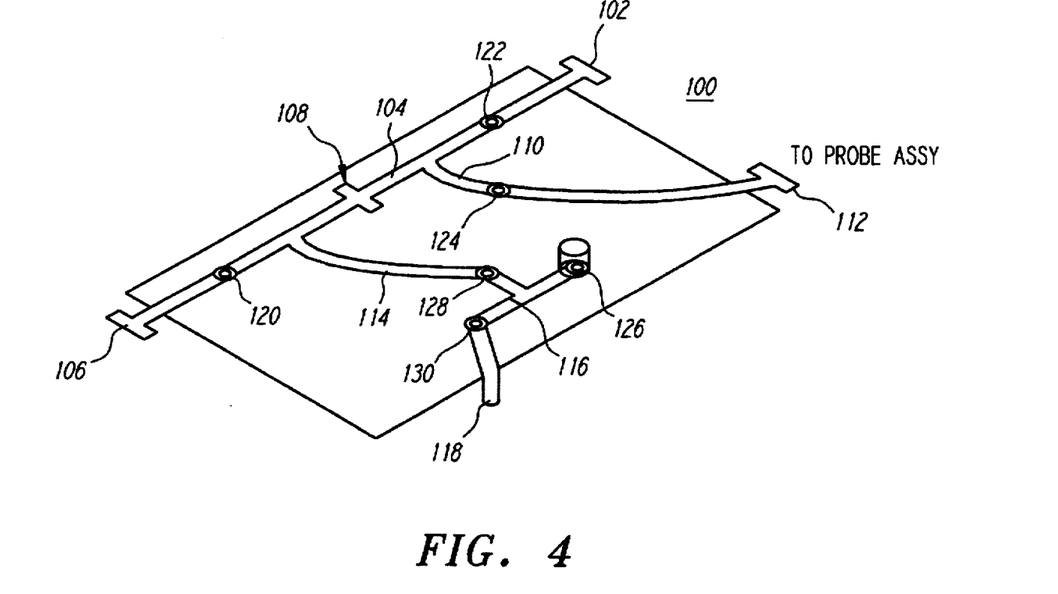
FIG. 4 shows a perspective view of an integrated manifold.

FIG. 4 shows a perspective view of an integral manifold assembly. The manifold 100 is preferably formed from plastic, such as polycarbonate, ABS, SAN, Styrolite™, or other suitable material which is sterilizable, preferable gamma sterilizable. The tubing is preferably a material which does not promote heparin binding (e.g., a teflon tube, or PVC or polyurethane tube with covalently linked heparin). Tubing size is selected to prevent hemolysis of the blood. A patient port 102 is connected to a fluid pathway 104 which couples to a fluid port 106. A detector 108 is optionally located on the fluid pathway 104. A sample line 110 is coupled to the fluid pathway 104, terminating in a analyzer interface port 112. A pump connection 114 connects to the fluid pathway 104. A pump force is supplied to vacuum region 116. The vacuum force in vacuum region 116 may be supplied by any known manner consistent with this invention, including but not limited to use of a peristaltic pump, a vacutainer, or a linear pump or a vacuum pump such as formed through a syringe having a linear force applied to the syringe. Optionally, if the vacuum force is generated by a vacutainer, a spike 118 may be utilized to interface the vacutainer. The spike 118 may also serve as a connection for disposal. A upstream isolation valve 120, a patient shut-off valve 122, a analyzer access valve 124, a disposal valve 126 and pump force valve 128 are utilized as described in connection with the similarly named valves in FIG. 2. A vacuum valve 130 optionally provides selective interconnection of the vacuum source with the manifold 100.

The feedback controlled delivery of heparin occurs in a "data poor" environment. Measurements of patient status cannot be obtained on a frequent basis. In the preferred embodiment, the infusion rate calculated by the control algorithm is based on a pharmacodynamic (PD) model of the heparin response. Since there is a large patient variability with heparin, there are a number of parameters in the PD model which describe the individual response. Based on measurements of patient response, the model parameters can be adjusted. Since the measurements are sparse and subject to some uncertainty, the patient parameter estimates will have a certain confidence interval which will affect the expected control accuracy. The information utilized includes population parameter values, including values of the variance and values for measurement accuracy. Sample scheduling may be optimized, though the system imposes certain limits on the frequency of measurement (such as cost and limited number of cartridges). The control system optionally determines when additional information from a new measurement would be most beneficial based upon observed patient response, history of infusion adjustment, desired control level accuracy, and confidence of model parameters.

Figure 5:
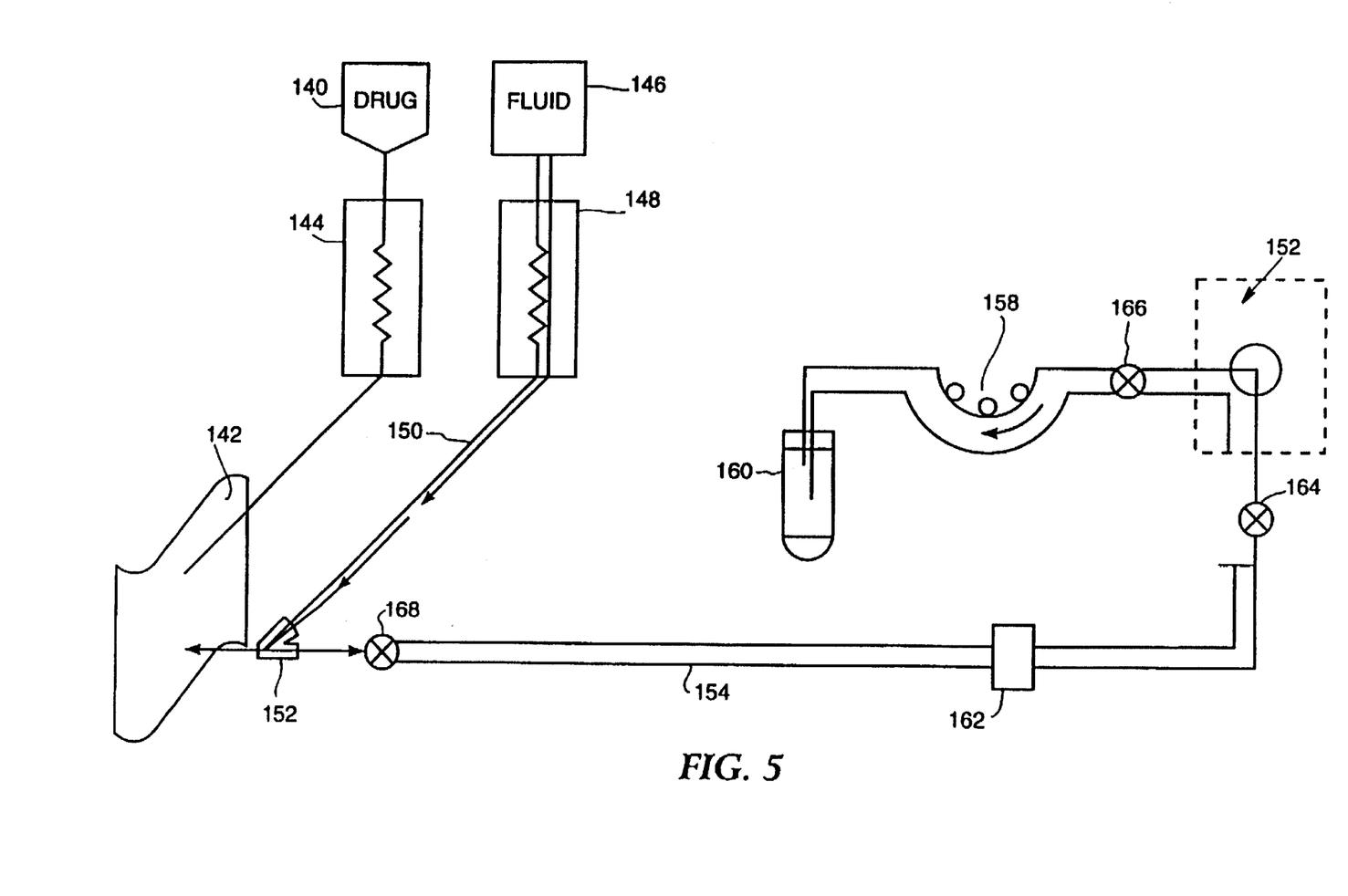
FIG. 5 shows an alternate fluidic system.

FIG. 5 shows a schematic view of an alternative fluidics arrangement to those shown in FIGS. 2 and 3. The drug source 140 is controllably connected to the patient arm 142 via pump 144, as described previously. The fluid source 146 is selectively connected to the patient arm 142 through pump 148. Delivery tube fluidic path 150 is connected to the patient arm 142, preferably via a Y-connector 152. The Y-connector 152 additionally connects to the sample path 154. The sample path 154 is operatively connected to the sampler system 156. A vacuum force is supplied to sample path 154, such as by operation of a peri-pump 158. Disposal is by any means desired, such as through a vacutainer 160. Optionally, a detector 162 may be utilized, in the preferred embodiment the detector 162 as shown comprising an optical window for use in conjunction with an optical detector. A sample system valve 164 serves to isolate the sample path 154 from the sampler system 156. A pump valve 166 serves to isolate the pump force, such as created by the peri-pump 158 from the sampler system 156.

In operation, sampling occurs by terminating drug delivery and flowing fluid from the fluid source 146 through the pump 148, through the Y-connector 152 through the sample path 154. Optionally, a check valve or electronically controlled valve is used. The fluid flow is aided by pump force a supplied by the pump 158, with valves 164 and 166 being open. The pump 148 is then turned off, resulting in the drawing of patient blood. Optionally a check valve 168 is utilized to control the fluid and blood flow. The blood is then pumped through the sample path 154. When the blood passes detector 162 the system may utilize that time and pump rate to calculate the necessary pumping time to cause delivery of blood to the sampler system 156. Once the sample has been delivered to the sampler system 156, flow of saline via the pump 148 may be utilized to provide a flushing source of fluid from the source 146 through the sample path 154. Once the sample is delivered to the sampler system 156, it may be analyzed and the data used in the feedback controlled control system.

Figure 6A:
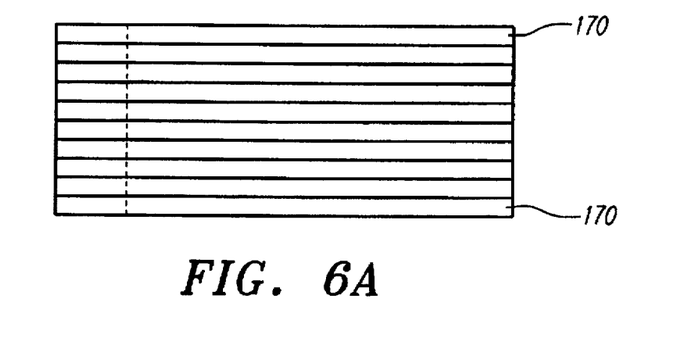
FIG. 6A shows a end-on view of a stacked multiple test unit system.

FIG. 6A shows a side view of multiple stack test units. Each test unit 170 comprises a test site 172 onto which the biological material to be analyzed is supplied. This test may include any of the desired tests, such as for monitoring of the coagulation state the APTT test such as manufactured by Boehringer Mannheim Diagnostics, Cardiovascular Diagnostics Inc. or International Technidyne Corporation. Alternative tests include the activated clotting time (ACT), Factor X or Xa, partial thromboplastin time tests, whole blood clotting time tests, or any general heparin assay.

Figure 6B:
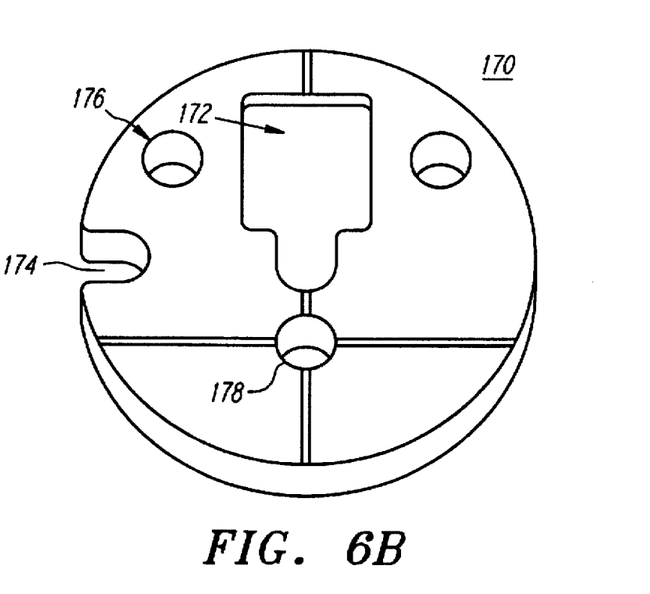
FIG. 6B shows a perspective view of an individual test disk for use in a multiple test unit.

Optionally, the test unit 170 may include a key way 174 to assist in orientation of the unit 170 during loading. Optionally, nesting dimples 176 may be provided to promote stacking of the test disks 170. A blood drop opening 178 may be provided for access to the test location 172.

Figure 7:
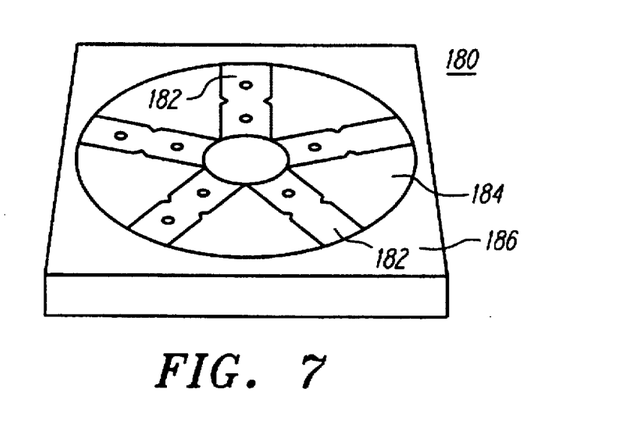
FIG. 7 shows a perspective view of a planar carousel arrangement for multiple test site locations.

FIG. 7 shows a perspective view of a planar carousel arrangement comprising multiple test units. A carousel 180 includes multiple test units 182 (five being shown in FIG. 7). The individual test units 182 are arranged symmetrically around an axis of rotation for the carousel 180. The individual test units 182 are mounted on a platten 184 which permits rotation of the platten relative to the housing 186.

Figure 8A:
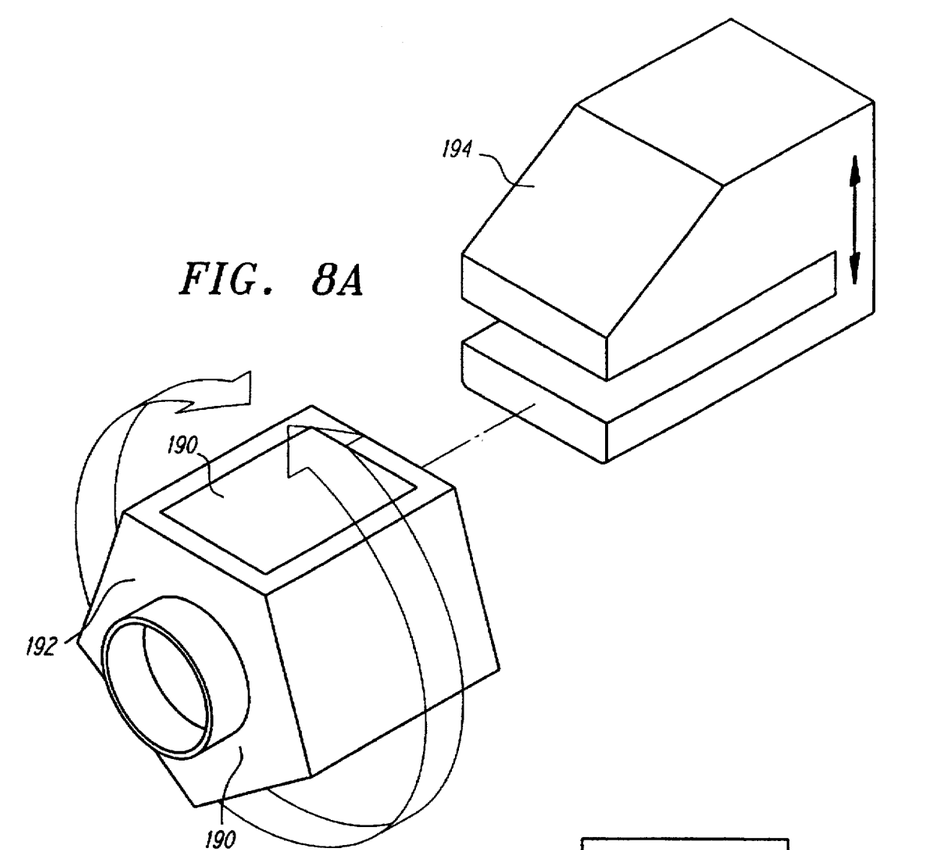
FIG. 8A shows a perspective view of a multiple test site location carousel.
Figure 8B:
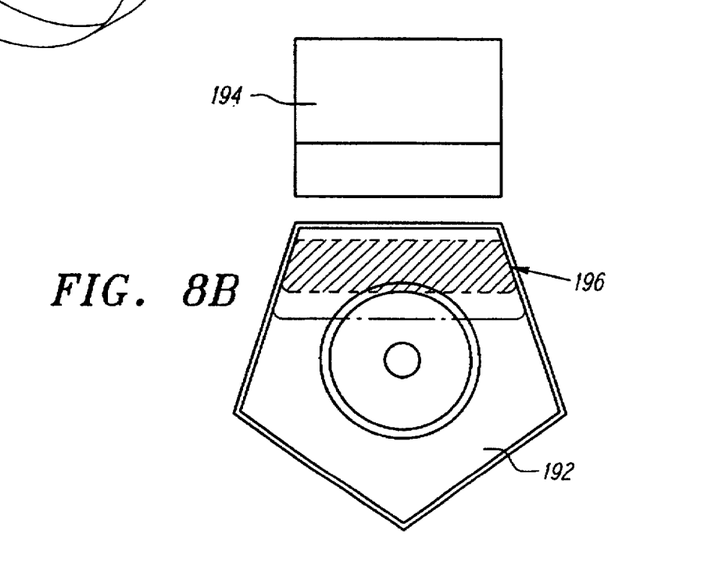
FIG. 8B shows an end-on view of the structure of FIG. 8A.

FIGS. 8A and 8B show views of an alternative arrangement for providing multiple test units to a detector. Test units 190 are affixed to a housing 192 presenting sequential faces to a reader head 194. In the embodiment shown, the cartridge 192 includes five faces on which test units 190 may be disposed. The cartridge 192 has a access of rotation permitting sequential apposition of a test unit 190 with the reader head 194. An arrow indicates the rotational motion of the cartridge 192 relative to the reader head 194. Optionally, a heater 196 may be utilized to aid in the testing process as performed by the test unit 190.

Figure 9A:
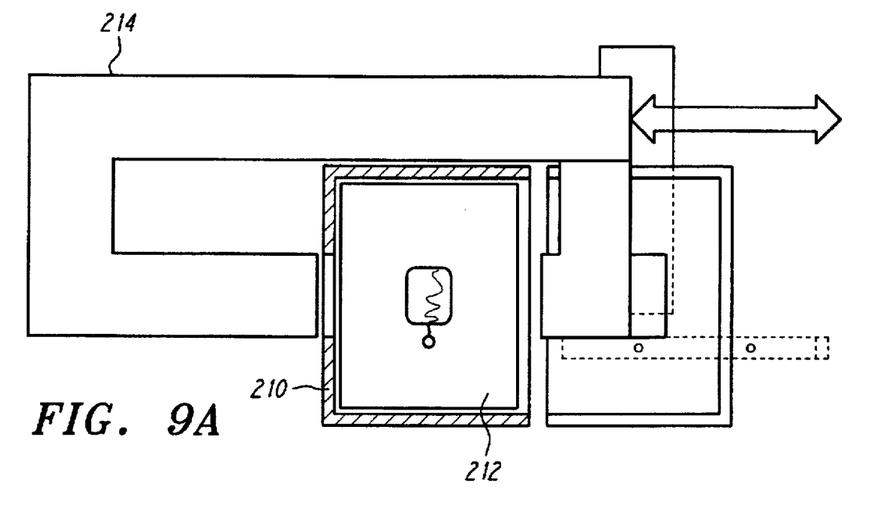
FIG. 9A shows a slidetray arrangement in top view.
Figure 9B:
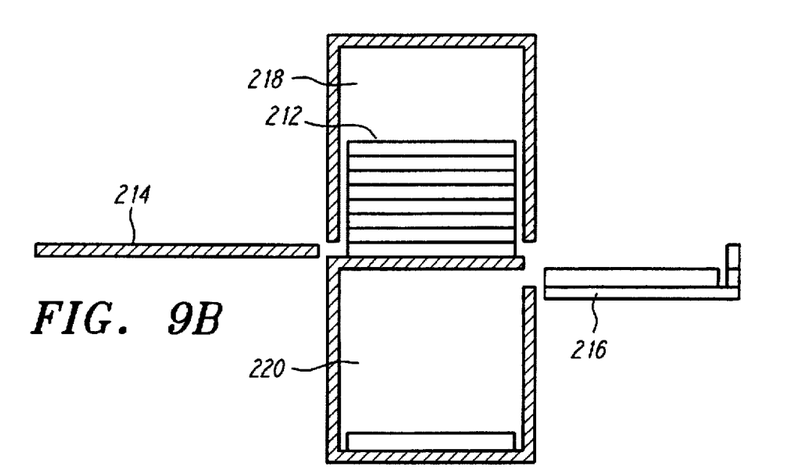
FIG. 9B shows a slidetray arrangement in side view.

FIGS. 9A and 9B show a top view and side view of a multiple test cartridge container. A cartridge 210 serves to contain multiple individual test chips 212. The cartridge 210 serves to contain the chips 212 in a stacked arrangement. An arm 214 causes displacement of the chip 212 from the cartridge 210 to a test stage 216. The chip 212 on the test stage 216 receives a blood drop upon which analysis is performed. Once the test is completed, the chip 212 is reinserted into the cartridge 210. Preferably, the cartridge 210 is formed with two chambers, an upper chamber 218 which contains the unused chips 212 and a lower chamber 220 who contains the used chips 212. The used chip 212 is removed from the test stage 216 by optional lowering of the test stage 216 relative to the cartridge 210, with optional lateral force applied to the chip 212 to cause the used chip to be inserted into the lower chamber 220.

Figure 10:
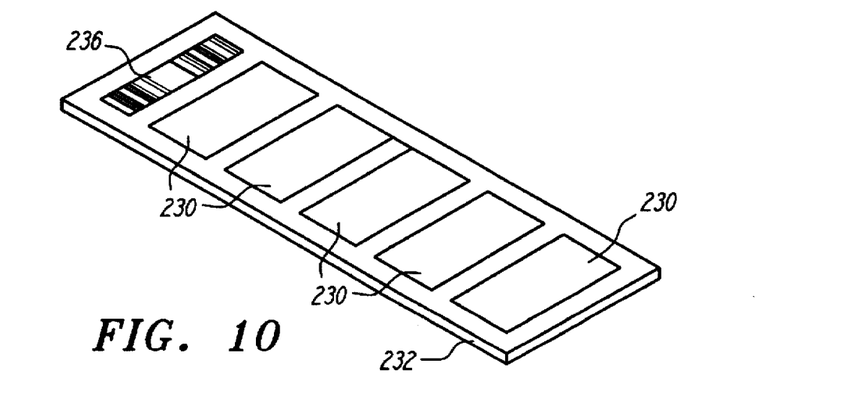
FIG. 10 shows a perspective view of a line of test cartridges and bar code.

FIG. 10 shows a perspective view of a multiple test cartridge system in which multiple individual test locations 230 are disposed laterally adjacent one another. Each individual test location 230 may be mounted on a substrate 232 or merely formed adjacent to each other, resulting in a unitary structure. Optionally, a bar code 234 is disposed on the multiple test cartridge system. In one embodiment, the bar code 234 may contain information indicative of the specific activity of the tests. For example, if aPTT tests are utilized in such a system, the tests tend to vary from manufacturer to manufacturer, and are even subject to different results being reported by different operators. The automated system of this invention permits the encoding of information (such as through the bar code) to indicate to the system the amount by which the test results must be corrected so as to provide a standardized result.

In one aspect of this invention, the system may be provided with test units to measure both the coagulation state (such as through the use of an aPTT test) and the prothrombin (PT) time. Such combinations are particularly useful when a patient is being transitioned from a heparin IV administration to Warfarin, during which time the aPTT measurements are affected by the presence of the Warfarin. Difficulty in titration of heparin is incurred at this time. By providing separate measurements of PT and aPTT, the system may correct for the presence of Warfarin and administer desirable amounts of heparin, and determine the optimum dose of Warfarin.

Although the invention has been described with respect to specific preferred embodiments, many variations and modifications may become apparent to those skilled in the art. It is therefore the intention that the appended claims be interpreted as broadly as possible in view of the prior art to include all such variations and modifications.

We claim:

1. A feedback controlled drug delivery system for delivering a fluid to a patient, the system comprising:

an input for receiving the fluid, an infusion pump connected to the input for receiving the fluid to control delivery of the the fluid as regulated by the pump, an analyzer adapted to receive a patient sample, and an interconnection between the fluid pump, the patient and the analyzer, the interconnection comprising:
   an interconnect input adapted for receiving the fluid and connected to the pump,
   an interconnect output connected to the patient for outputting the fluid to the patient,
   a fluid pathway formed between the interconnect input and the interconnect output, and
   a connection between the fluid pathway and the analyzer.

2. The feedback controlled drug delivery system of claim 1 wherein the interconnect output is further adapted to receive the patient sample as input.

3. The feedback controlled drug delivery system of claim 1 wherein the patient sample is blood.

4. The feedback controlled drug delivery system of claim 1 further including a drug input operatively connected to the interconnect input and under control of the system.

5. The feedback controlled drug delivery system of claim 1 wherein the fluid is heparin.

6. The feedback controlled drug delivery system of claim 1 wherein the fluid is selected from the group consisting of: Hirudin, Hirulog, and direct thrombin inhibitors.

7. The feedback controlled drug delivery system of claim 1 wherein the fluid is a IIb/IIIa antagonist.

8. The feedback controlled drug delivery system of claim 7 wherein the analyzer is a platelet aggregation assay or IIb/IIIa assay.

9. The feedback controlled drug delivery system of claim 1 further including an interlock adapted to positively interconnect between a predefined drug source and the remainder of the system.

10. A method for sampling blood in an automated sampling system having a non-drug fluid port connected to a non-drug fluid source, a patient port adapted for providing non-drug fluid to the patient and, alternatively, drawing blood from the patient, the non-drug fluid port and the patient port being connected by a fluid pathway, a first valve operatively connected to the fluid pathway to selectively isolate the patient from the fluid pathway, a sample pathway selectively connectable to the fluid pathway via a second valve, and an analyzer connected to the sample pathway, the steps comprising:

1. filling the fluid pathway to the patient with non-drug fluid,
   2. drawing the non-drug fluid away from the patient so as to draw the patient's blood into the fluid pathway; to a point past the sample pathway,
   3. isolating the patient from the sample pathway by closing the first valve,
   4. opening the second valve to permit blood to pass into the sample pathway, and
   5. moving the blood through the sample pathway to the analyzer.

11. The method of claim 10 wherein the blood is moved through the sample pathway to the analyzer by the step of flowing non-drug fluid through the non-drug fluid port into the fluid pathway.

12. The method of claim 10 wherein the blood is moved through the sample pathway to the analyzer by the step of pumping blood through the sample pathway to the analyzer.

13. The method of claim 10 wherein step 2 a detector generates a signal indicating that the blood has moved in the fluid pathway to a point past the sample pathway.

14. The method of claim 13 wherein the signal generated by the detector is utilized to cause termination of the drawing of the patient's blood further through the fluid pathway.

15. A feedback controlled drug delivery device for adjusting the quantity of a fluid delivered to a patient in response to analysis of a sample taken from the patient, comprising:

a fluid pump receiving the fluid from a fluid source, a fluid line creating a fluid path between the fluid pump and the patient;

an analyzer, a sample line connecting the fluid line to the analyzer, creating a sample path between the patient and the analyzer, a pressure means operatively associated with the analyzer for drawing the sample from the patient to the analyzer, and a controller communicating with the analyzer and controlling the fluid pump and the pressure means.

16. A feedback controlled drug delivery device for regulating the quantity of a fluid delivered to a patient by adjusting the volumetric flow from a controllable fluid source in response to analysis of a sample taken from the patient, comprising:

a fluid tube creating a fluid path between the controllable fluid source and the patient, an analyzer operatively connected to a sample drawing function, a sample tube connecting the fluid tube to the analyzer, a controller communicating with the analyzer and controlling the controllable fluid source and the sample drawing function.

17. A feedback controlled drug delivery device, comprising:

a controllable drug or non-drug fluid source for providing a fluid, an analyzer for accepting a patient sample, a fluid line invasively attached to a patient and connected to the controllable drug or non-drug fluid source and the analyzer, a controller communicating to the controllable drug or non-drug fluid source and the analyzer wherein fluid flows into the fluid line and alternately the patient sample flows out the fluid line.

\* \* \* \* \*